(12) United States Patent
Watts et al.

(10) Patent No.: US 6,310,089 B1
(45) Date of Patent: Oct. 30, 2001

(54) COMPOSITION FOR THE ADMINISTRATION OF A D1-AGONISTS

(75) Inventors: Peter James Watts; Lisbeth Illum, both of Nottingham (GB)

(73) Assignee: West Pharmaceutical Services Drug Delivery & Clinical Research Centre Limited, Nottingham (GB)

( * ) Notice: Subject to any disclaimer, the term of this patent is extended or adjusted under 35 U.S.C. 154(b) by 0 days.

(21) Appl. No.: 09/475,680

(22) Filed: Dec. 30, 1999

(30) Foreign Application Priority Data

Dec. 31, 1998 (GB) .................................................. 9828861

(51) Int. Cl.$^7$ .................................................. A61K 31/38
(52) U.S. Cl. ............................................ 514/444; 514/443
(58) Field of Search ...................................... 514/443, 444

(56) References Cited

U.S. PATENT DOCUMENTS 5,597,832 * 1/1997 Michaelides et al. ............... 514/285

FOREIGN PATENT DOCUMENTS

WO 89/03207 4/1989 (WO) .

OTHER PUBLICATIONS

Benoit, et al., "Biodegradable Microspheres: Advances in Production Technology" in *Microencapsulation—Methods and Industrial Applications*, pp. 35–72, (Benita, ed.), Dekker:New York, 1996.

Farraj, et al., "Nasal administration of insulin using bioadhesive microspheres as a delivery system," *J. Cont. Rel.* 13:253–261 (1990).

Felmeister, "Powders" in *Remington's Pharmaceutical Sciences*, 15$^{th}$ Edition, pp. 1554–1575, Mack:Philadelphia, 1975.

Gill, et al., "Intranasal absorption of granulocyte–colony stimulating factor (G–CSF) from powder formulations, in sheep," *Eur. J. Pharm. Sci.* 6:1–10 (1998).

Lindberg, et al., "Biodegradable starch microspheres—A new medical tool," *Microspheres and Drug Therapy*, pp. 153–188, (Davis, et al.) Elsevier:Amsterdam, 1984.

Thompson, "Cyclodextrins—enabling excipients: their present and future use in pharmaceuticals," *Crit Rev Ther Drug Carrier Syst.* 14(1):1–104 (1997).

* cited by examiner

*Primary Examiner*—Dwayne C. Jones
(74) *Attorney, Agent, or Firm*—Holland & Knight LLP

(57) ABSTRACT

A composition for intranasal administration comprising a full or partial D1-agonist of the dopamine receptor.

23 Claims, 1 Drawing Sheet

COMPOSITION FOR THE ADMINISTRATION OF A D1-AGONISTS

CROSS REFERENCES TO RELATED APPLICATIONS

Priority is claimed under 35 U.S.C. §119 to GB 9828861.6 filed Dec. 31, 1998.

FIELD OF THE INVENTION

The present invention relates generally to the nasal delivery of dopamine agonists and, more particularly, to a composition for the nasal delivery of D1-agonists for the treatment of Parkinson's disease.

DESCRIPTION OF THE RELATED ART

Parkinson's disease is a neurological disorder where there is a progressive loss of dopamine secreting neurons. Dopamine agonists can be used to rectify this loss via interaction with dopamine receptors. There are different families of these receptors, the D1 and D2 families, the D1 family being further subdivided.

Levodopa (L-DOPA or dihydroxypenylalanine) is a well-known and effective treatment for Parkinson's disease. Other drugs for treating the disease include selegiline, bromocriptine and lisuride.

All existing dopaminergic therapies have significant therapeutic properties and are either non-selective or D2-selective. A selective D1 receptor agonist that was acceptable clinically would be most advantageous.

D1 partial agonists, such as SKF 38393 and CY208.243 have been evaluated, but with inconclusive results.

ABT-431 represents a new approach to treating Parkinson's disease that has been shown to be effective in clinical studies when administered by injection. The efficacy compares well with that of oral levodopa. (Brefel et al., Poster Presented at the 7th International Parkinson's Disease Symposium, London, March 1997).

ABT-431 is a mixture of three chemically related hydrochloride salt prodrugs and the hydrochloride salt of the active entity A-86929. The hydrochloride salt of the diacetyl prodrug is termed A-93431.1 and comprises greater than 95% of the mixture. All four compounds making up ABT-431 are rapidly converted to the active form A-86929 in vivo and is then further degraded or metabolised. A-86929 is a selective full agonist of dopamine D1 receptors. A-93431.1 (FIG. 1) is (−)-trans9,10-diacetyloxy-2-propyl-4,5,5a,6,7,11b-hexahydro-3-thia-5-azacyclopent-1-ena[c]phenanthrene hydrochloride. A-86929.1 (FIG. 2) is (−)-trans9,10-dihydroxy-2-propyl-4,5,5a,6,7,11b-hexahydro-3-thia-5-azacyclopent-1-ena[c]phenanthrene hydrochloride.

ABT-431 is also understood to have other effects due to its D1-agonist nature. These include improved cognition in debilitating diseases such as Alzheimer's disease and in the control of substance abuse. The dose of the drug ABT-431 will be selected with such therapeutic applications in mind.

Solid formulations of ABT-431 can be prepared that have acceptable shelf stability. However, when these are given to animals as oral products, the extent of absorption is low as measured by the bioavailability as compared to an intravenous control. Such low and erratic absorption would be unsuitable for the treatment of Parkinson's patients.

It would be advantageous if ABT-431 and similar compounds could be given by a transmucosal route. However, the poor solubility of ABT-431 in water and its inherent instability suggests that transmucosal delivery would be problematical.

BRIEF SUMMARY OF THE INVENTION

The present applicant has developed a new composition for nasal administration comprising a full or partial D1-agonist of the dopamine receptor. The composition may allow for the effective administration of ABT-431 and related compounds via the nasal route for the treatment of Parkinson's disease, cognition and substance abuse.

DETAILED SUMMARY OF THE INVENTION

Figure 1:
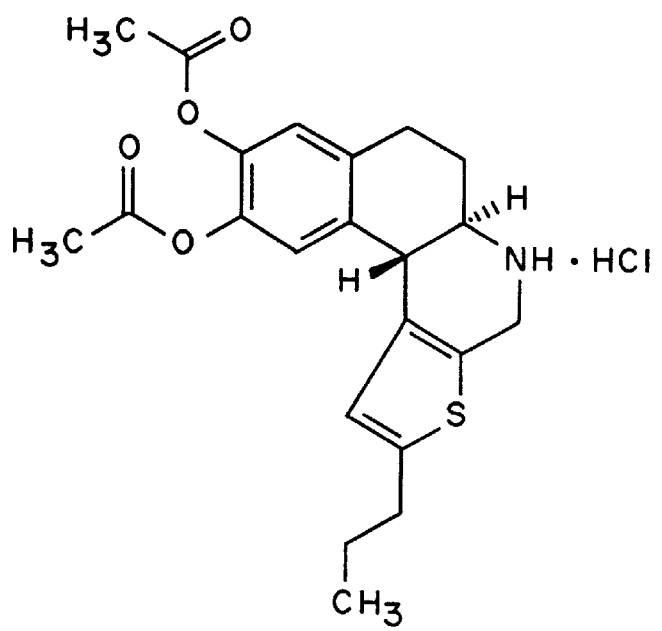
FIG. 1 is a schematic of A-93431.1.
Figure 2:
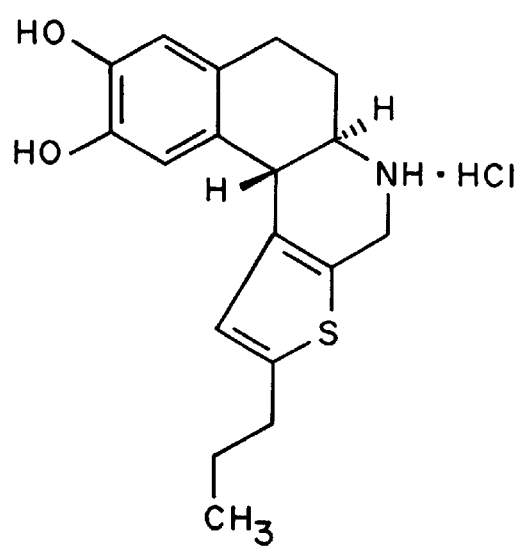
FIG. 2 is a schematic of A-86929.1.

According to the present invention, there is provided a composition for the intranasal administration of a full or partial D1-agonist of the dopamine receptor.

The present applicant has found surprisingly that D1-agonists such as ABT-431 can be administered via the nasal route and that by such means it is possible to achieve a bioavailability of greater than 5% and more often greater than 10% in animal models as well as in a Phase I study in human subjects.

By the term bioavailability, we mean the absorption of the drug into the systemic circulation as measured by the area under the plasma level versus time profile as compared to the area under the plasma level versus time profile for a reference in the form of an intravenous injection.

D1-agonists of the dopamine receptor for use in the composition of the present invention include A-86929 or its prodrug moiety A-93431. A mixture of the chemically related hydrochloride salts of the prodrug and the hydrochloride salt of the active entity A-86929, known as ABT-431, may also be used. Related compounds, by which we mean D1-agonists that are partial and full agonists at the dopamine D1 receptor in assays in vitro, may also be used, such as SKF 38393 and CY208.243.

The compositions may be in the form of powders or microspheres, and may also be bioadhesive in nature.

By a powder, we mean a fine dispersion of solid material that can be irregular in shape. (Fehmuster, Remington's Pharmaceutical Sciences, 15th Edition, Mack, Philadelphia, 1975, p1554). Such powders can be produced by a variety of methods, including attrition, e.g. milling of a solid material.

Microspheres are specialised solid particles that can be produced by methods such as spray drying, emulsification or phase separation (see Davis et al., Microspheres and Drug Therapy, Elsevier, Amsterdam, 1984 and Benoit et al., Microencapsulation—Methods and Industrial Applications, Benita, Dekker, New York, 1996, p35).

By a bioadhesive material, we mean a material that can interact with a mucosal surface such as that found in the nose.

The compositions typically comprise a mixture of the full or partial D1-agonist with an excipient material.

Pharmaceutical excipients suitable for use in the present composition include polysaccharides, polymers or mixtures of these materials.

Polysaccharides suitable for use in the present composition include, inter alia, starches, modified starches, chitosan, pectin, gellan, xanthan, microcrystalline cellulose, hydroxypropylcellulose, carboxymethylcellulose, alginates, dextrans and polygalactosamine. The polysaccharides may be in the form of powders or microspheres.

Starches that are suitable for use in the present composition include soluble starch (amylodextrin) as well as starches modified with ethylene oxide (hydroxyethyl starch).

The polysaccharides can be in the form of powders or microspheres.

An especially preferred polysaccharide excipient are cross-linked starch microspheres, particularly those described in GB-1518121, the disclosure in which is incorporated herein by way of reference. The microspheres in GB-1518121 are produced by the emulsion polymerization of a soluble potato starch hydrolysate to give microspheres which are then cross-linked, e.g. by means of epichlorohydrin. Further details can be found in Lindbergh et al., Microspheres and Drug Therapy, Davis et al., Elsevier, Amsterdam, 1984, p 153, the disclosures in which are incorporated herein by way of reference.

The cross-linking process renders the starch microspheres water insoluble. However, the microspheres will absorb water and swell. On intranasal administration, the microspheres absorb water on contact with the mucosal layer. This can result in adhesion and prolong the residence time of the microspheres in the nasal cavity.

Preferred polymer excipients are the (meth)acrylate copolymers, with Eudragit® types RL and RS (Röhm Pharma, Darmstadt, Germany) being particularly preferred and Eudragit® RL being especially preferred. These materials are copolymers of acrylic and methacrylic acid esters with a low content of quaternary ammonium groups. Eudragits® RL and RS are referred to in the United States Pharmacopoeia/National Formulary as ammonio methacrylate copolymers.

Eudragits® RL and RS have been found to possess properties that can make their inclusion in nasal powder compositions desirable. Firstly, they can act as oil-in-water stabilisers in an emulsion spray drying process. As a result, the drug and polymer can be dissolved in an organic solvent such as dichloromethane and emulsified into an external aqueous phase to form a stable emulsion which can then be spray-dried. Secondly, they are positively charged in the pH range 2–8 owing to the presence of the quaternary ammonium groups.

A bioadhesive effect may be achieved through the interaction of the positively charged polymer with the negatively charged surface of the cells lining the nasal mucosa, or by the interaction of a positively charged polymer with the negative sugar groups in mucin.

The excipient may be at least partially constituted by a material which functions as a solubilising agent for the D1-agonist. Suitable solubilising agents include the cyclodextrins and derivatives thereof.

Cyclodextrins for use as pharmaceutical excipients have been described in Thompson, Crit. Rev. Ther. Drug Carrier Syst., 14, 1 (1997). They include alpha, beta and gamma cyclodextrins. Derivatised cyclodextrins may also be used. For example, beta cyclodextrins may be derivatised to form materials such as dimethyl beta cyclodextrin, hydroxypropyl beta cyclodextrin and sulphocyclodextrins such as sulphobutyl ether cyclodextrins. The preferred cyclodextrin is alpha cyclodextrin.

The ratio of excipient to drug, on a weight basis, is preferably in the range of from 1:20 to 20:1, more preferably in the range of from 1:10 to 10:1 and most preferably in the range of from 1:5 to 5:1.

The composition of the invention may be prepared by mixing the drug or prodrug with the excipient in an aqueous or organic solvent to provide a solution or suspension. The solvent can then be removed by an established process such as freeze drying (for aqueous systems) or spray drying (for systems containing aqueous and organic based solvents) to provide the required composition.

The drug or prodrug may be dissolved in an appropriate solvent before it is added to the solution or suspension of the excipient. Suitable solvents for dissolving the drug or prodrug include dichloromethane and ethanol.

Alternatively, the drug may be dissolved in a solution of a solubilising agent. Suitable solubilising agents include the cyclodextrin and derivatives thereof.

The cyclodextrins may be used at concentrations of from 0.1 to 20% w/v. A concentration of from 1 to 5% w/v cyclodextrin is preferred for alpha cyclodextrin. By concentration in w/v, we mean the weight of cyclodextrin in grams (g) dissolved in 100 ml of water or aqueous solution.

Where cyclodextrin is used, the preferred ratio of cyclodextrin to drug in the final composition, on a weight basis, is in the range of from 1:20 to 20:1, more preferably in the range of from 1:10 to 10:1 and most preferably in the range of from 1:5 to 5:1.

In yet another method for preparing the pharmaceutical composition, an oil-in-water emulsion is prepared, which is then spray dried. The oil phase of the emulsion comprises a water-immiscible organic solvent, examples of which include dichloromethane and ethyl acetate. The D1-agonist is dissolved in the oil phase together with a copolymer of acrylic acid and methacrylic acid esters. Preferred (meth)acrylate copolymers are Eudragits® types RL and RS, most preferably Eudragit® type RL. The drug containing oil phase is then emulsified into a larger volume of an aqueous phase in which there may optionally be dissolved an inert excipient to provide additional powder mass or to improve powder flow properties. Examples of such excipients include polysaccharides. The copolymer of acrylic acid and methacrylic acid esters acts to stabilise the resulting oil-in-water emulsion and is typically present in the organic solvent phase at a concentration in the range 0.05 to 10% w/v, preferably 0.075% to 7.5% w/v and most preferably 0.1 to 5% w/v. The emulsion is then processed using a spray-drier to remove the water and organic solvent and leave a powder comprising microparticles comprising the D1-agonist, the copolymer of acrylic acid and methacrylic acid esters and, optionally, additional excipient(s).

The above method for preparing a pharmaceutical composition by spray drying an oil-in-water emulsion may be applied to the preparation of pharmaceutical compositions comprising a drug other than a D1-agonist.

The quantity of the composition administered to the nose may be from 1 to 100 mg, preferably from 5 to 75 mg and more preferably from 10 to 50 mg.

The dose of drug that can be administered to the nose may be from 0.5 to 90 mg, preferably from 2 to 50 mg and more preferably from 5 to 40 mg.

An especially preferred composition comprises a lyophilised mixture of the D1-agonist, cyclodextrin and cross-inked starch microspheres. The composition preferably contains 1 to 45 weight % of the D1 agonist, 1 to 45 weight % cyclodextrin and 10 to 98 weight % cross-linked starch microspheres. More preferably, the composition contains 3 to 40 weight % of the D1-agonist, 3 to 40 weight % cyclodextrin and 20 to 94 weight % cross-linked starch microspheres, and most preferably contains 5 to 35 weight % drug, 5 to 35 weight % cyclodextrin and 30 to 90 weight % starch microspheres.

The composition of the invention can be administered to the nose of man or a mammal using any suitable nasal administration device. Such devices are well described in the prior art and include nasal insufflators, the Bespak powder devices, Direct-Haler® system valois Monopoudre®.

The present invention is now illustrated but not limited with reference to the following examples.

A series of A-93431.1 formulations were prepared in order to evaluate which would provide good absorption (i.e. high bioavailability via the nasal route) and good stability. Some of these formulations were used as control or reference formulations and do not form part of this invention.

EXAMPLE 1

Simple Solution Formulations (Control)

A solution formulation (Formulation A) was prepared by dissolving 150 mg of A-93431.1 (Abbott Laboratories, USA) in 2.5 ml of ethanol in a 10 ml volumetric flask. To the flask was added 6 ml of water, the contents adjusted to pH 7.4 using 0.1 M sodium hydroxide solution and the volume was made up to 10 ml with water.

EXAMPLE 2

Chitosan Solution Formulation

A second solution formulation (Formulation B), containing the cationic absorption enhancer chitosan, was prepared. A chitosan stock solution was prepared by dissolving 100 mg of chitosan glutamate (SeaCure G210, Pronova, Norway) in 8 ml of water, adjusting to pH 4 using 0.1 M hydrochloric acid and making the volume up to 10 ml with water. In a beaker, 5 ml of chitosan stock solution, 1 ml of water and 2.5 ml of ethanol were mixed together. To this mixture was added 150 mg of A-93431.1. When the A-93431.1 had dissolved, the beaker contents were adjusted to pH 4, transferred to a 10 ml volumetric flask and made up to volume with water.

EXAMPLE 3

Formulation Based on Starch Microspheres

A solution containing 15 mg/ml of alpha cyclodextrin was prepared by dissolving 150 mg of alpha cyclodextrin (Sigma Chemicals, UK) in 10 ml of water. 150 mg of A-93431.1 was weighed into a 100 ml wide-necked flask. To the flask was added 10 ml of the alpha cyclodextrin solution to solubilise the A-93431.1 and 300 mg of cross-linked starch microspheres (Eldexomer®, Perstorp Pharma, Sweden). The suspension of microspheres in drug solution was adjusted to pH 4 using 0.1 M hydrochloric acid and then frozen by immersing the flask in liquid nitrogen. The frozen suspension was lyophilised for 16 hours using an Edwards Modulyo freeze-drier. The lyophilised powder (Formulation C) was transferred to a glass bottle for storage.

EXAMPLE 4

Formulation Based on Hydroxyethyl Starch

In a 500 ml beaker, 3.125 g of hydroxyethyl starch (Leopold Pharma, Austria) was dissolved in 200 ml of water. In a 100 ml beaker, 1.5 g of A-93431.1 and 0.375 g of Eudragit RL100 (Röhm Pharma, Germany) were dissolved in 50 ml of dichloromethane. This solution was added to the hydroxyethyl starch solution and the two were mixed together for 12 minutes using a Silverson L4R high speed homogeniser, alternating between speed settings 5 and 10. The resulting emulsion was then spray-dried using a Lab Plant SD4 spray-drier (drying temperature 169° C., exhaust temperature 72–81° C., atomising pressure 1.9 bar, air flow setting 22, pump speed 10 ml/min) to produce a fine, white powder (Formulation D).

EXAMPLE 5

Formulation Based on a Methacrylate Based Polymer

In a 500 ml beaker, 3.125 g of mannitol (Fisher Scientific, UK) was dissolved in 200 ml of water. In a 100 ml beaker, 1.5 g of A-93431.1 and 0.375 g of Eudragit RL100 (Röhm Pharma, Germany) were dissolved in 50 ml of dichloromethane. This solution was added to the mannitol solution and the two were mixed together for 1 minute using a Silverson L4R high speed homogeniser, alternating between speed settings 5 and 10. The resulting emulsion was then spray-dried using a Lab Plant SD4 spray-drier (drying temperature 169° C., exhaust temperature 72–81° C., atomising pressure 1.9 bar, air flow setting 22, pump speed 10 ml/min) to produce a fine, white powder (Formulation E).

EXAMPLE 6

Formulation for Intravenous Dosing (Control)

A formulation for intravenous administration (Formulation F) containing 0.6 mg/ml A-93431.1 was prepared by weighing 120 mg of A-93431.1 into a 200 ml volumetric flask. The drug was dissolved by adding 150 ml of 5% dextrose solution. The flask contents were made up to volume with 5% dextrose solution.

EXAMPLE 7

Evaluation of Formulations in an Animal Model

The pharmacokinetic performance of Formulations A to F was evaluated in a single group of six sheep after intranasal administration using the 5 methods described in PCT/GB88/00836, Gill et al. (Eur. J. Pharm. Sci., 6, 1998) and Farraj et al. (J. Cont. Rel., 13, 253, 1990). A wash-out period of at least four days was allowed between the administration of each formulation. Formulations A to E were administered intranasally at an A-93431.1 dose of 0.3 mg/kg. Formulation F was administered by intravenous infusion at an A-93431.1 dose of 0.3 mg/kg. Plasma samples were collected from an indwelling jugular cannula and assayed by HPLC for drug content. The mean bioavailability of each formulation was calculated relative to the intravenous dose. These data are presented in the table below.

TABLE 1

Pharmacokinetic performance of Formulations A to E

| Formulation | Bioavailability (% vs. IV) |
|---|---|
| A | 34.3 |
| B | 63.0 |
| C | 117.1 |
| D | 64.6 |
| E | 63.1 |

Compared to the control nasal solution (Formulation A), all of the other formulations showed improved bioavailability of A-93431.1. Formulation C (lyophilised powder), which contained alpha cyclodextrin and starch microspheres, showed the best performance.

EXAMPLE 8

Stability

In order for a nasal product to be suitable for commercial development it must demonstrate good stability so far as the drug is concerned as well as good bioavailability.

The stability of Formulations A to E (Examples 1 to 5) was assessed. The formulations were stored at 4° C., 25° C./60% RH (RH=relative humidity) and 40° C./75% RH and then analysed for A-93431.1 content and the concentration of the two monoester degradation products at time 0, 3 weeks and 6 weeks. Data (recovery of A-93431.1 at 3 and 6 weeks relative to Time 0) are presented in the table below:

TABLE 2

Recovery of A-93431.1 after stability testing

| Formulation | 4° C. | 25° C./60% RH | 40° C./75% RH |
|---|---|---|---|
| A-3 weeks | 100.6 | 95.8 | 79.3 |
| A-6 weeks | 99.6 | 82.9 | 53.5 |
| B-3 weeks | 100.9 | 88.3 | 63.2 |
| B-6 weeks | 98.8 | 69.4 | 21.2 |
| C-3 weeks | 100.6 | 101.3 | 94.9 |
| C-6 weeks | 96.3 | 93.8 | 96.2 |
| D-3 weeks | 94.8 | 87.7 | 85.8 |
| D-6 weeks | 94.3 | 86.4 | 88.2 |
| E-3 weeks | 86.5 | 83.1 | 77.6 |
| E-6 weeks | 82.1 | 78.5 | 71.4 |

The loss of A-93431.1 was generally accompanied by an increase in the amount of monoester. The stability study indicated that the solution formulations (A and B) were particularly unstable. The powder formulations showed much better stability, with the greatest loss of drug being measured in the spray-dried mannitol powder (Formulation E). Formulation C containing the drug together with alpha cyclodextrin and starch microspheres demonstrated the best stability.

EXAMPLE 9

Preparation of Formulation C for study in man

Formulation C, which gave a good bioavailability in the sheep model when administered nasally and also demonstrated good stability, was examined in a clinical trial. 15 g of alpha cyclodextrin (Alpha W6, Wacker Chemie) was dissolved in 1500 ml of purified water. 15 g of A-93431.1 (Abbott Laboratories, Chicago) was added to the cyclodextrin solution and then stirred until dissolved. The cyclodextrin-drug solution was passed through a 0.2 μm membrane filter and added to 30 g of cross-linked starch microspheres (Eldexomer®). The suspension was divided as 25 ml aliquots into 60×70 ml glass injection vials. The vials were part-stoppered and transferred to an Edwards EF10/10 freeze-drier. After 96 hours, the vials were sealed and removed from the freeze-drier. The contents of each vial were transferred onto a 0.5 mm sieve. The powder mass was passed through the sieve, transferred to a bottle, placed onto a roller-mixer (Denley Spiramix) and mixed for 5 minutes. The mixture was then filled into polypropylene capsules for nasal inhalation (Bespak, King's Lynn, UK) at a fill weight of 40 mg, equivalent to 9.2 mg of A-93431.1 (6.44 mg of A-86929.0 equivalents) per capsule.

EXAMPLE 10

Phase 1 Clinical Study with Formulation C

The capsules prepared in Example 9 were administered to a group of healthy human volunteers. On separate occasions groups of volunteers received, in an escalating dose fashion, one, two or four capsules (9.2 mg, 18.4 mg and 36.8 mg of A-93431.1, respectively). Each volunteer also received an intravenous (IV) infusion containing 7.1 mg of A-93431.1. Plasma samples were collected over a ten hour period and analysed for A86929.0 content using an HPLC method. The bioavailability was calculated relative to the IV infusion. The mean bioavailability of the 9.2 mg, 18.4 mg and 36.8 mg doses was 36%, 24% and 21% relative to the intravenous dose, respectively.

What is claimed is:

1. A composition for intranasal administration in the form of a powder or microspheres comprising a full or partial D1-agonist of the dopamine receptor wherein the full or partial D1-agonist of the dopamine is taken up by mucosal absorption.

2. The composition of claim 1 wherein the D1-agonist is the prodrug (−)-trans-9,10-diacetyloxy-2-propyl-4,5,5a,6,7,11b-hexahydro-3-thia-5-azacyclopent-1-ena[c]phenanthrene or the active moiety (−)-trans-9,10-dihydroxy-2-propyl-4,5,5a,6,7,11b-hexahydro-3-thia-5-azacyclopent-1-ena[c]phenanthrene or a mixture of the hydrochloride salts of the prodrug and the hydrochloride salt of the active entity (ABT-431).

3. The composition of claim 1 wherein the D1-agonist is mixed with a pharmaceutical excipient.

4. The composition of claim 3 wherein the excipient comprises a bioadhesive material.

5. The composition of claim 3 wherein the excipient is selected from the group consisting of polysaccharides, polymers, and combinations thereof.

6. The composition of claim 3 wherein the excipient comprises a material selected from the group consisting of chitosan, starches, microspheres, (meth)acrylate copolymers, gellan, alginate, pectin, xanthan, and microcrystalline cellulose.

7. The composition of claim 6 wherein the excipient comprises starch microspheres.

8. The composition of claim 7 wherein the starch microspheres are cross-linked.

9. The composition of claim 8 wherein the excipient comprises a solubilising agent.

10. The composition of claim 9 wherein the solubilising agent is a cyclodextrin.

11. The composition of claim 10 wherein the cyclodextrin is a α-cyclodextrin.

12. The composition of claim 3 wherein the excipient comprises a solubilising agent.

13. The composition of claim 12 wherein the solubilising agent is a cyclodextrin.

14. The composition of claim 13 wherein the cyclodextrin is α-cyclodextrin.

15. The composition of claim 1 in the form of a freeze dried powder.

16. The composition of claim 1 in the form of a spray dried powder.

17. The composition of claim 1 made by a process comprising the steps of (a) making an oil-in-water emulsion in which the D1-agonist is located in the oil phase and the emulsion is stabilised by the use of a copolymer of acrylic acid and methacrylic acid esters and (b) spray drying the emulsion.

18. A method for treating a patient in need of treatment with a full or partial D1-agonist, the method comprising administering intranasally a composition in the form of a powder or microspheres comprising a full or partial D1-agonist of the dopamine receptor wherein the full or partial D1-agonist of the dopamine is taken up by mucosal absorption.

19. The method of claim 18 wherein the patient is in need of treatment of Parkinson's disease, cognition or substance abuse.

20. A method for preparing a pharmaceutical composition comprising a drug, the method comprising
   (a) making an oil-in-water emulsion in which the drug is located in the oil phase, wherein the emulsion is stabilised by the use of a copolymer of acrylic acid and methacrylic acid esters; and
   (b) spray drying the emulsion.

21. The method of claim 20 wherein the drug comprises a full or partial D1-agonist of the dopamine receptor.

22. A device for administering a full or partial D1-agonist to a patient comprising a nasal administration device having a composition in the form of a powder or microspheres comprising a full or partial D1-agonist of the dopamine receptor wherein the full or partial D1-agonist of the dopamine is taken up by mucosal absorption.

23. A method of delivering a full or partial D1-agonist to a patient comprising administering intranasally to the patient a composition in the form of a powder or microspheres comprising a full or partial D1-agonist of the dopamine receptor wherein the full or partial D1-agonist of the dopamine is taken up by mucosal absorption.

* * * * *